(12) United States Patent
Joye et al.

(10) Patent No.: US 6,846,798 B2
(45) Date of Patent: Jan. 25, 2005

(54) POLYALKOXYLATED TERPENIC COMPOUNDS, THEIR PROCESS OF PREPARATION AND THEIR USE AS DEFOAMING AGENTS

(75) Inventors: Jean-Luc Joye, Cranbury, NJ (US); Agnes Froute, Neuilly sur Seine (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 10/176,455

(22) Filed: Jun. 20, 2002

(65) Prior Publication Data

US 2003/0054972 A1 Mar. 20, 2003

Related U.S. Application Data

(63) Continuation of application No. 09/947,784, filed on Sep. 7, 2001, now abandoned, which is a continuation of application No. 09/331,131, filed on Nov. 8, 1999, now abandoned, which is a continuation of application No. PCT/FR97/02381, filed on Dec. 22, 1997.

(30) Foreign Application Priority Data

Dec. 20, 1996 (FR) .......................................... 96 15712

(51) Int. Cl.[7] ............................................. C11D 1/722
(52) U.S. Cl. ................................................. 510/506
(58) Field of Search .............................. 510/102, 506

(56) References Cited

U.S. PATENT DOCUMENTS

| 3,370,080 A | 2/1968 | Bloch .......................... 260/457 |
| 4,450,307 A | 5/1984 | Moss .......................... 568/665 |
| 5,674,823 A | 10/1997 | Ricca .......................... 510/102 |
| 5,817,885 A | 10/1998 | Ricca .......................... 568/612 |

FOREIGN PATENT DOCUMENTS

WO    WO 96/01245    1/1996   ......... C07C/43/178

OTHER PUBLICATIONS

International Search Reprot.

*Primary Examiner*—John R. Hardee

(57) ABSTRACT

The invention concerns polyalkoxylated terpenic compounds of formula $Z-X-W-[CH(R^5)-CH(R^6)-O]_q-A$ in which Z is a bicycloheptenyl or bicycloheptyl radical, preferably substituted by methy radicals; X is preferably a $-CH_2-CH_2-O$ or $O-CH_2-CH_2-O-$ radical; W is a polysequence, preferably polyoxypropylene and polyoxyethylene; $[CH(R^5)-CH(R^6)-O]_q$ is a sequence different from a polyoxyethylene sequence, preferably polyoxypropylene; A is H, a functional or hydrocarbon group. They can be prepared by successively polyalcoxylating the reagent Z-XH. They can be used as antifoaming agents in foaming aqueous media, in particular in degreasing aqueous media in alkaline medium of sheet metals, as well as detergent aqueous media in household washing or industrial and institutional washing.

6 Claims, 3 Drawing Sheets

POLYALKOXYLATED TERPENIC COMPOUNDS, THEIR PROCESS OF PREPARATION AND THEIR USE AS DEFOAMING AGENTS

This application is a continuation application of application Ser. No. 09/947,784 filed on Sep. 07, 2001, now ABN which is a continuation application of application Ser. No. 09/331,131 filed on Nov. 08, 1999. Now ABN which is a continuation of PCT/FR97/02381, filed Dec. 22, 1997.

The subject-matter of the present invention is novel polyalkoxylated terpenic compounds, their process of preparation and their use as defoaming agents for foaming aqueous media, the term "terpenic" signifying "of terpenic origin".

It is known, from International Application WO 96/01245, that polyalkoxylated bicycloheptane or bicycloheptene terpenic derivatives in which the polyalkoxy group comprises a polyoxyethylene block and/or a polyoxypropylene block are surface-active agents which do not foam very well.

It has now been found that polyalkoxylated bicycloheptane or bicycloheptene terpenic derivatives in which the polyalkoxy group comprises at least one polyoxyethylene block and at least two higher polyoxyalkylene blocks (in particular polyoxypropylene blocks), one of the said higher polyoxyalkylene blocks being at the chain end of the said polyalkoxylated terpenic derivatives, not only do not foam very well but, in addition, exhibit outstanding properties of defoaming foaming aqueous media.

A first subject-matter of the invention consists of novel polyalkoxylated terpenic compounds of formula (I)

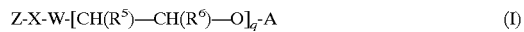

in which formula:

the Z symbol represents a bicyclo[a.b.c]heptenyl or bicyclo[a.b.c]heptyl radical, optionally substituted by at least one $C_1-C_6$ alkyl radical, preferably a methyl radical, a, b and c being such that:

$a+b+c=5$, $a=2$, 3 or 4, $b=1$ or 2, $c=0$ or 1, the X symbol represents a group

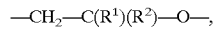

or 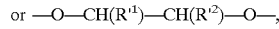

the $R^1$ and $R^2$ symbols being identical or different and representing a linear or branched $C_1-C_6$ (cyclo)alkyl or (cyclo)alkenyl group, in particular a methyl group, or preferably a hydrogen atom, the $R'^1$ and $R'^2$ symbols being identical or different and representing a linear or branched $C_1-C_{22}$ (cyclo)alkyl or (cyclo)alkenyl group, in particular a methyl group, or preferably a hydrogen atom, the $R^5$ and $R^6$ symbols are different, one representing a hydrogen atom and the other a linear or branched $C_1-C_{22}$ (cyclo)alkyl or (cyclo)alkenyl group, preferably a methyl group, q is a mean value which can range from 1 to 30, preferably from 5 to 20, W represents a polyblock group composed of different $-[B]_n-$ and $-[C]_p-$ blocks, B representing a $—CH(R^3)—CH(R^4)—O—$group, in which $R^3$ and $R^4$ are identical or different and represent a hydrogen atom or a linear or branched $C_1-C_{22}$ (cyclo)alkyl or (cyclo)alkenyl group, preferably a methyl group, $R^3$ and $R^4$ being different when one of them represents hydrogen, C representing an oxyethylene group $—CH_2—CH_2—O-$ (EO), n being a mean value which can range from 1 to 10, preferably from 2 to 4, p being a mean value which can range from 1 to 100, preferably from 3 to 20, the said polyblock group W being bonded to the X unit by one of its $-[B]_n-$ blocks, A represents a hydrogen atom, a $C_1-C_6$ alkyl radical, an aryl or alkylaryl radical, a halogen atom, a $—CH_2—CH(OH)R^7$ group, where the $R^7$ symbol represents a linear or branched or cyclic $C_1-C_{22}$ alkyl radical or an aryl radical, or a group chosen from $—SO_3M$, $—OPO_3(M)_2$, $—(CH_2)_a—COOM$ or $—(CH_2)_b—SO_3M$, with a and b ranging from 1 to 6 and M representing H, Na, K, Li or $N(RR'R''R''')^+$, where the R, R', R'' and R''' symbols are identical or different and represent a hydrogen atom or an optionally hydroxylated linear or branched or cyclic $C_1-C_{22}$ alkyl radical.

Figure 1:
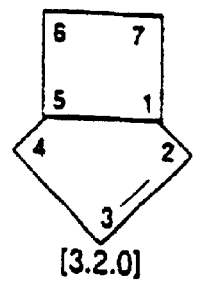
FIGS. 1 and 2 represent the backbones of the Z symbol in formula (I).
Figure 1:
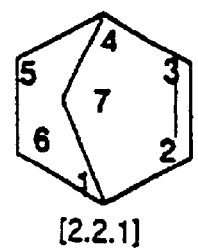
Figure 1:
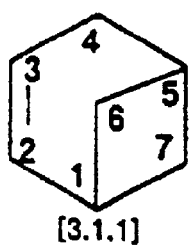
Figure 1:
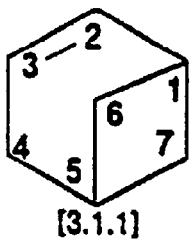
Figure 1:
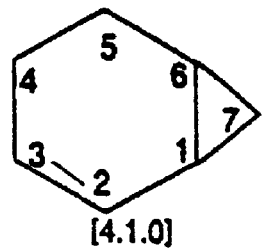
Figure 1:
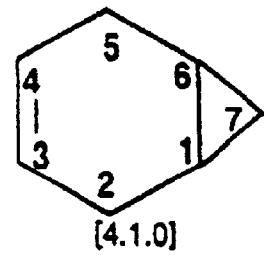
Figure 2:
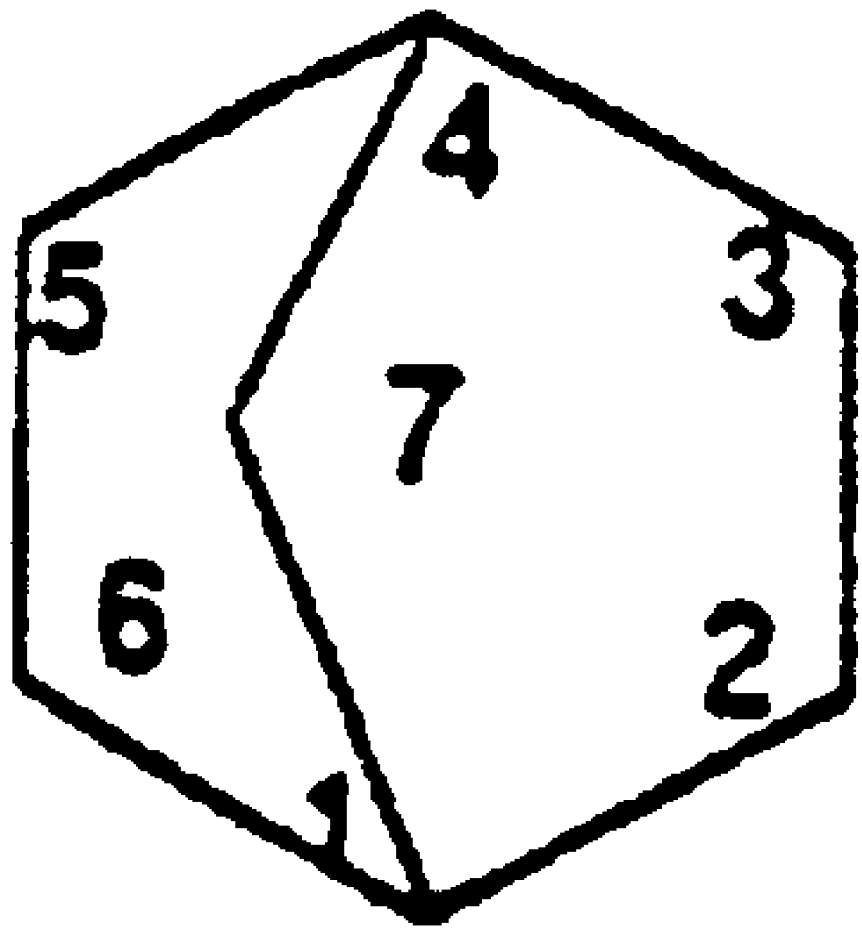

A representation of the unsubstituted bicyclo[a.b.c] heptene and unsubstituted bicyclo[a.b.c]-heptane Z backbones is given in FIGS. 1 and 2.

The Z symbol preferably represents a $Z^1$ or $Z^2$ radical, $Z^1$ being
a bicyclo[3.1.1]heptenyl radical, preferably substituted on its carbon atom at the 6-position by at least one $C_1-C_6$ alkyl radical, very particularly by two methyl radicals, the said bicyclo[3.1.1]heptenyl radical being bonded to the X unit of formula $—CH_2—C(R^1)(R^2)—O—$ via its carbon atom at the 2-position;

or a bicyclo[2.2.1]heptenyl radical, preferably substituted on its carbon atom at the 7-position by at least one $C_1-C_6$ alkyl radical, very particularly by two methyl radicals, the said bicyclo[2.2.1]heptenyl radical being bonded to the X unit of formula $—CH_2—C(R^1)(R^2)—O—$ via its carbon atom at the 2-position or at the 3-position;

$Z^2$ being a bicyclo[2.2.]heptyl radical, preferably substituted on its carbon atom at the 7-position by at least one $C_1-C_6$ alkyl radical, very particularly by two methyl radicals, the said bicyclo[2.2.]heptyl radical being bonded to the X unit of formula $—O—CH(R'^1)—CH(R'^2)—O—$ via its carbon atom at the 2-position or at the 3-position.

The said $[B]_n$ and $[CH(R^5)—CH(R^6)—O]_q$ blocks are preferably $[PO]_n$ and $[PO]_q$ polyoxypropylene blocks.

In a very particularly preferred way, the W symbol represents a $-[B]_n-[C]_p-$ diblock group, the $[B]_n$ block being a $[PO]_n$ polyoxypropylene block and the $[C]_p$ block being an $[EO]_p$ polyoxyethylene block.

The subject-matter of the present invention is more particularly the novel polyalkoxylated terpenic compounds of formula $Z^1\text{-}CH_2\text{—}CH_2\text{—}O\text{-}[PO]_n\text{-}[EO]_p\text{-}[PO]_q\text{-}A$ or $Z^2\text{-}O\text{—}CH_2\text{—}CH_2\text{—}O\text{-}[PO]_n\text{-}[EO]_p\text{-}[PO]_q\text{-}A$ $Z^1$ and $Z^2$ having the definition given above.

Mention may in particular be made, as examples of these novel compounds, of those of formula

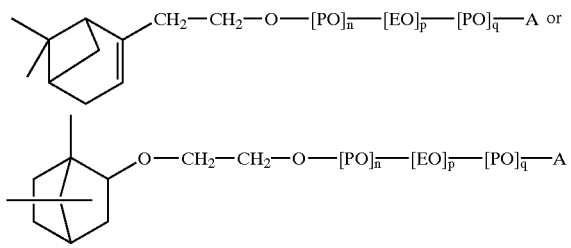

The mean values of n, p and q are preferably chosen so that a 1% by weight solution in distilled water of the said compound exhibits a cloud point of less than 40° C.

The compounds forming the subject-matter of the invention can be prepared by successive polyalkoxylation reactions of the reactant of formula Z-XH with at least two different types of alkoxylation agent, one of which is ethylene oxide and the other or others of which is/are a higher alkylene oxide, with final alkoxylation using a higher alkylene oxide and then optional functionalization of the terminal hydrogen atom.

More specifically, the said Z-XH reactant is subjected to successive polyalkoxylation reactions with alkylene oxide (AO1) of formula

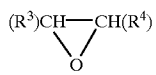

ethylene oxide (EO) of formula

and alkylene oxide (AO2) of formula

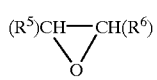

$R^3$, $R^4$, $R^5$ and $R^6$ having the definition given above, with
successive introduction of the alkylene oxides (AO1) and (EO) and final introduction of alkylene oxide (AO2),
in order to obtain a product of formula $Z\text{-}X\text{-}W\text{-}[CH(R^5)\text{—}CH(R^6)\text{—}O]_qH$ in which W and q have the definition given above, and then optionally functionalization in order to convert the terminal hydrogen atom into one of the A substituents, other than hydrogen, as defined above.

Thus, the novel polyalkoxylated terpenic compounds of formula (I) forming the subject-matter of the invention, in which formula X represents —$CH_2$—$C(R^1)(R^2)$—O—, can be obtained by polyalkoxylation reaction of a reactant of formula (I')

$Z\text{-}CH_2\text{—}C(R^1)(R^2)OH$         (I')

in which the Z, $R^1$ and $R^2$ symbols have the definition given above, with alkylene oxide (AO1) of formula

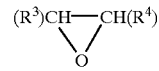

ethylene oxide (EO) of formula

and alkylene oxide (AO2) of formula

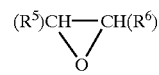

$R^3$, $R^4$, $R^5$ and $R^6$ having the definition given above, with
successive introduction of the alkylene oxides (AO1) and (EO) and final introduction of alkylene oxide (AO2),
in order to obtain a product of formula $Z\text{-}CH_2\text{—}C(R^1)(R^2)\text{—}O\text{-}W\text{-}[CH(R^5)\text{—}CH(R^6)\text{—}O]_qH$ in which W and q have the definition given above, and then optionally functionalization in order to convert the terminal hydrogen atom into one of the A substituents, other than hydrogen, as defined above.

The novel polyalkoxylated terpenic compounds of formula (I) forming the subject-matter of the invention, in which formula X represents —O—$CH(R'^1)$—$CH(R'^2)$—O—, can be obtained by polyalkoxylation reaction of a reactant of formula (I'')

$Z\text{-}O\text{—}CH(R'^1)\text{—}CH(R'^2)\text{—}OH$         (I'')

in which the Z, $R'^1$ and $R'^2$ symbols have the definition given above, with alkylene oxide (AO1) of formula

ethylene oxide (EO) of formula

and alkylene oxide (AO2) of formula

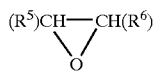

$R^3$, $R^4$, $R^5$ and $R^6$ having the definition given above, with successive introduction of the alkylene oxides (AO1) and (EO) and final introduction of alkylene oxide (AO2), in order to obtain a product of formula

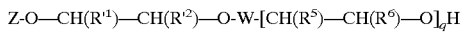

in which W and q have the definition given above, and then optionally functionalization in order to convert the terminal hydrogen atom into one of the A substituents, other than hydrogen, as defined above.

The methods for preparation of the reactants of formulae (I') and (I") are disclosed in International Application WO 96/01245.

In a very particularly preferred way, the reactants of formulae (I') and (I") have the formulae (II') and (II")

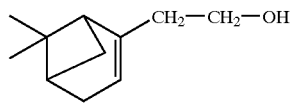

known as "Nopol", obtained by reaction of β-pinene with formaldehyde;

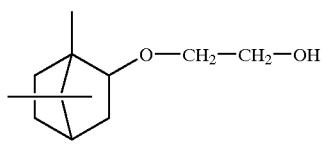

known as "Arbanol", obtained by isomerization of α-pinene to camphene and then ethoxyhydroxylation.

The alkylene oxides (AO1) and (AO2) are preferably propylene oxide.

The polyalkoxylation reactions are carried out according to well-known methods at a temperature greater than 100° C., preferably between 120 and 250° C., very particularly between 150 and 200° C., in the presence of a catalyst (strong bases, aliphatic amines, Lewis acids). The operation is advantageously carried out in the presence of an inert gas (nitrogen) or of a rare gas (argon or carbon monoxide), preferably at a pressure of the order of 1 to 4 bar. This type of reaction is given in greater detail in International Application WO 96/01245.

The alkylene oxide (AO1) and the ethylene oxide (EO) are introduced successively, before the final introduction of the alkylene oxide (AO2). The amounts of alkylene or ethylene oxide employed correspond to the numbers of molar equivalents n, p and q desired. The conditions for carrying out such a procedure are well known to a person skilled in the art.

The optional functionalization operation for converting the terminal hydrogen atom into one of the other A substituents can be, for example, an etherification or esterification operation on the terminal hydrogen atom; this stage is well known per se; it is preferably carried out after neutralization.

Thus, the following preparations can be carried out:

of ether sulphates (A=—$SO_3M$), according to the procedure disclosed in GB 1,111,208 or U.S. Pat. No. 3,392,185 of ether phosphates (A=—$OPO_3(M)_2$), according to the procedure disclosed in U.S. Pat. No. 3,331,896 of ether carboxylates (A=—$(CH_2)_a$—COOM), according to the procedure disclosed in U.S. Pat. No. 2,623,900 or U.S. Pat. No. 2,983,738 of ether sulphonates (A=—$(CH_2)_b$—$SO_3M$), according to the procedure disclosed in U.S. Pat. No. 2,115,192, U.S. Pat. No. 4,978,780 or K. Suga, Austr. J. Chem., 21, 2333 (1968)

or of alkyl ethers (A=alkyl), according to the procedure disclosed in U.S. Pat. No. 2,913,416.

These methods of functionalization are disclosed in greater detail in WO 96/01245.

Another subject-matter of the present invention is the use as defoaming agent, in aqueous media capable of forming foams, of at least one polyalkoxylated terpenic compound of formula (I) as defined above.

The aqueous media, for which it is necessary to limit the volume of foam which can be formed during their use, are in particular aqueous media for degreasing metal sheets in alkaline medium, aqueous media for degreasing drilling platforms, aqueous media employed for cleaning oil drilling wells drilled by means of oil-based fluids, and aqueous detergent media used in household detergency (washing machines, dishwashers, washing of hard surfaces) or in industrial and institutional detergency.

During the use of aqueous media for degreasing metal sheets in alkaline medium, the formation of foam can result from the presence in the degreasing composition of foaming detergent surface-active agents, as well as the presence of soaps resulting from fatty acids or from esters present in the contaminating medium to be removed.

These same difficulties can appear during the degreasing of oil platforms. It should be noted that, in the field of oil exploitation, the foaming can also be caused by the presence of foaming compounds in the crude oil. The phenomenon of foaming is very often dangerous in this specific application. Thus, in addition to the obvious problems of safety present on platforms which have become slippery, the creation of foam in the well itself, during the operation of cleaning the latter before the latter is brought into production, has the consequence of decreasing the relative density in the well (by inclusion of air) and can, for example, result in the uncontrolled eruption of the oil if it is a gusher.

During the use of aqueous detergent media in household detergency or in industrial and institutional detergency, the appearance of foam can be due to the presence, in the detergent composition, of foaming detergent surface-active agents, as well as to the presence of certain residues, such as food proteins of the albumin type, milk, and the like.

The said defoaming agent according to the invention can be employed in the aqueous medium, for which it is necessary to limit the volume of foam formed, either via degreasing or detergent compositions, by introduction of the said agent into the said compositions at the time of the manufacture of the latter or by introduction of the said agent into the said compositions at the time of use of the latter, or alternatively by direct addition of the said agent to the aqueous medium for which it is necessary to limit the volume of foam formed.

The latter is employed according to amounts which are a function of the amount of foaming agent(s) present in the aqueous medium and of the foaming power of the latter.

In aqueous media for degreasing metal sheets in alkaline medium, the said defoaming polyalkoxylated terpenic agents can be generally present in a proportion of the order of 0.01 to 5 g/l, preferably of the order of 0.1 to 1 g/l, of the said medium.

In the field of oil exploitation, more particularly the degreasing of platforms, the aqueous media comprise of the order of 0.005 to 0.05 g/l, preferably of the order of 0.015 to 0.025 g/l, of the said medium (after dilution) of defoaming polyalkoxylated terpenic agents.

For what relates more particularly to the cleaning of the well, the amount of defoaming agent is employed with a concentration of between 0.5 and 10% by weight in the aqueous solution, preferably 1 to 5%.

In the field of washing-machine household detergency, amounts of defoaming polyalkoxylated terpenic agents of the order of 2 to 10%, preferably of the order of 3 to 5%, by weight with respect to the dry content of the detergent medium, for a conventional detergent formulation containing of the order of 5 to 15% of anionic and/or nonionic surface-active agents, are recommended. In dishwasher household detergency, these amounts can be of the order of 0.5 to 10%, preferably of the order of 1 to 3%.

In the aqueous media used in industrial and institutional detergency, the said defoaming polyalkoxylated terpenic agents can be generally present in a proportion of the order of 0.005 to 0.05 g/l, preferably of the order of 0.015 to 0.025 g/l, of the said medium (after dilution).

The degreasing or detergent aqueous media comprising the said defoaming agent of the invention are preferably used at a temperature at least of the order of their cloud temperature.

Another subject-matter of the present invention is the degreasing or detergent compositions comprising at least one polyalkoxylated terpenic compound of formula (I) as defined above.

The formulations for degreasing metal sheets in alkaline medium additionally comprise:

of the order of 0 to 2%, generally of 0.01 to 1%, by weight (in the aqueous solution) of at least one anionic or nonionic detergent surface-active agent, such as ($C_8$–$C_{16}$) alkylbenzenesulphonates, ($C_8$–$C_{20}$)alkyl sulphates, ethoxylated alkylphenols, ethoxylated fatty alcohols, or block polymers of ethylene oxide and of propylene oxide, of the order of 5 to 20% by weight (in the aqueous solution) of at least one hydrotropic electrolyte, such as benzenesulphonates, mono- or di ($C_1$–$C_4$)alkylbenzenesulphonates, or toluene-, xylene- or cumenesulphonates, other hydrotropic agents, such as alcohols and glycols, of the order of 5 to 25% by weight (in the aqueous solution) of at least one sequestering agent, such as nitriloacetic acid, ethylenediaminetetraacetic acid, ethylenediaminetetramethylenephosphonic acid, nitrilotrimethylenephosphonic acid or their salts, buffer agents, such as alkanolamines, ethylene-diamine, and the like.

The aqueous compositions employed for the degreasing of oil platforms can comprise, in addition to the abovementioned polyalkoxylated terpenic compound:

of the order of 0 to 2%, generally of 0.01 to 1%, by weight (in the aqueous solution) of at least one anionic or nonionic detergent surface-active agent, such as ($C_8$–$C_{16}$) alkylbenzenesulphonates, ($C_8$–$C_{20}$) alkyl sulphates, ethoxylated alkylphenols, ethoxylated fatty alcohols, or block polymers of ethylene oxide and of propylene oxide, of the order of 5 to 20% by weight (in the aqueous solution) of at least one hydrotropic electrolyte; such as benzenesulphonates, mono- or di($C_1$–$C_4$) alkylbenzenesulphonates, or toluene-, xylene- or cumenesulphonates, other hydrotropic agents, such as alcohols and glycols, at least one agent for controlling the pH, such as, for example, alkali metal carbonates, sesquicarbonates or bicarbonates, additives, such as enzymes, in an amount which can range up to 5% of the total weight of the aqueous fluid, or agents for inhibiting the corrosion of metals.

The aqueous media employed for the cleaning of oil wells comprise, in addition to the polyalkoxylated terpenic compound:

3 to 40% by weight of the aqueous medium of surface-active agents, such as:

anionic surface-active agents, such as alkyl ester sulphonates of formula R—CH($SO_3$M)-COOR', where R represents a $C_{8\text{-}20}$, preferably $C_{10}$–$C_{16}$, alkyl radical, R' a $C_1$–$C_6$, preferably $C_1$–$C_3$, alkyl radical and M an alkali metal cation (sodium, potassium or lithium), a substituted or unsubstituted ammonium (methyl-, dimethyl-, trimethyl- or tetramethylammonium, dimethylpiperidinium, and the like) cation or a cation derived from an alkanolamine (monoethanolamine, diethanolamine, triethanolamine, and the like). Mention may very particularly be made of the methyl ester sulphonates for which the R radical is a $C_{14}$–$C_{16}$ radical;

alkyl sulphates of formula ROSO$_3$M, where R represents a $C_5$–$C_{24}$, preferably $C_{10}$–$C_{18}$, alkyl or hydroxyalkyl radical, M representing a hydrogen atom or a cation with the same definition as above, and their ethoxylated (EO) and/or propoxylated (PO) derivatives exhibiting an average of 0.5 to 30, preferably of 0.5 to 10, EO and/or PO units;

alkylamide sulphates of formula RCONHR'OSO$_3$M, where R represents a $C_2$–$C_{22}$, preferably $C_6$–$C_{20}$, alkyl radical, R' represents a $C_2$–$C_3$ alkyl radical, M representing a hydrogen atom or a cation with the same definition as above, and their ethoxylated (EO) and/or propoxylated (PO) derivatives exhibiting an average of 0.5 to 60 EO and/or PO units;

salts of saturated or unsaturated $C_8$–$C_{24}$, preferably $C_{14}$–$C_{20}$, fatty acids, $C_9$–$C_{20}$ alkylbenzenesulphonates, primary or secondary $C_8$–$C_{22}$ alkylsulphonates, alkylglycerol sulphonates, the sulphonated polycarboxylic acids disclosed in GB-A-1,082,179, paraffin sulphonates, N-acyl-N-alkyltaurates, alkyl phosphates, isethionates, alkylsuccinamates, alkylsulphosuccinates, the monoesters or diesters of sulphosuccinates, N-acylsarcosinates, alkylglycoside sulphates or polyethoxycarboxylates the cation being an alkali metal (sodium, potassium, lithium), a substituted or unsubstituted ammonium residue (methyl-, dimethyl-, trimethyl- or tetramethylammonium, dimethylpiperidinium, and the like) or a residue derived from an alkanolamine (monoethanolamine, diethanolamine, triethanolamine, and the like);

nonionic surface-active agents, such as polyoxyalkylenated (polyoxyethylenated, polyoxypropylenated or polyoxybutylenated) alkylphenols, the alkyl substituent of which is $C_6-C_{12}$, comprising from 5 to 25 oxyalkylene units; mention may be made, by way of example, of Triton X-45, Triton X-114, Triton X-100 or Triton X-102, sold by Röhm & Haas Co.;

glucosamides, glucamides or glycerolamides;

polyoxyalkylenated $C_8-C_{22}$ aliphatic alcohols comprising from 1 to 25 oxyalkylene (oxyethylene or oxypropylene) units; mention may be made, by way of example, of Tergitol 15-S-9 or Tergitol 24-L-6 NMW, sold by Union Carbide Corp., Neodol 45-9, Neodol 23-65, Neodol 45-7 or Neodol 45-4, sold by Shell Chemical Co., or Kyro EOB, sold by The Procter & Gamble Co.;

the products resulting from the condensation of ethylene oxide, the compound resulting from the condensation of propylene oxide with propylene glycol, such as the Pluronics sold by BASF;

the products resulting from the condensation of ethylene oxide, the compound resulting from the condensation of propylene oxide with ethylenediamine, such as the Tetronics sold by BASF;

amine oxides, such as ($C_{10}-C_{18}$ alkyl)dimethylamine oxides or ($C_8-C_{22}$ alkoxy)ethyldihydroxyethylamine oxides;

the alkylpolyglycosides disclosed in U.S. Pat. No. 4,565,647;

$C_8-C_{20}$ fatty acid amides;

ethoxylated fatty acids;

ethoxylated fatty amides;

ethoxylated amines;

amphoteric and zwitterionic surface-active agents, such as
alkyl dimethyl betaines, alkyl amidopropyldimethyl betaines, alkyl trimethyl sulphobetaines, or the condensation products of fatty acids and of protein hydrolysates;

alkyl amphoacetates or alkyl amphodiacetates in which the alkyl group comprises from 6 to 20 carbon atoms;

at least one agent making it possible to adjust the pH, such as, for example, alkali metal carbonates, sesquicarbonates or bicarbonates, alkali metal hydroxides or alkaline earth metal hydroxides;

additives, such as enzymes, in an amount which can range up to 5% of the total weight of the aqueous fluid, or agents for inhibiting the corrosion of metals, if necessary, weighting agents, so as to maintain a satisfactory hydrostatic pressure in the well:

Mention may be made, as examples of such compounds, of soluble or at least partially soluble salts, such as alkali metal or alkaline earth metal halides, such as sodium chloride, potassium chloride, caesium chloride, magnesium chloride, sodium bromide or potassium bromide. Use may likewise be made of alkali metal or alkaline earth metal sulphates, carbonates, bicarbonates, silicates or phosphates, alone or as a mixture. Mention may very especially be made, among salts of organic acids, of alkali metal or alkaline earth metal formates or alkali metal or alkaline earth metal acetates. Alkali metal or alkaline earth metal halides, and more particularly chlorides, are preferred. It is possible, although not preferred, to employ insoluble salts, such as alkaline earth metal sulphates, silicates or carbonates, such as barium sulphate or calcium carbonate; or alkaline earth metal or zinc bromides, such as potassium bromide, zinc bromide, and the like.

hydrocolloids, such as polysaccharides of vegetable origin, such as polygalactomannans and their derivatives, such as guar or hydroxypropylguar; cellulose and its derivatives, starches and their derivatives; or polysaccharides of bacterial origin, such as xanthan gum or deacetylated derivatives.

The detergent compositions for dishwashers generally comprise:

at least one surface-active agent in an amount which can range from 0.5 to 10%, preferably of the order of 1 to 5%, of the weight of the said detergent formulation expressed on a dry basis.

Mention may be made, among these, of:
anionic surface-active agents of the following type: alkali metal soaps (alkali metal salts of $C_8-C_{24}$ fatty acids), alkaline sulphonates ($C_8-C_{13}$ alkylbenzenesulphonates or $C_{12}-C_{16}$ alkyl-sulphonates), oxyethylenated and sulphated $C6-C_{16}$ fatty alcohols, oxyethylenated and sulphated $C_8-C_{13}$ alkylphenols, alkaline sulphosuccinates ($C_{12}-C_{16}$ alkylsulphosuccinates) and the like, nonionic surface-active agents of the following type: polyoxyethylenated $C_6-C_{12}$ alkylphenols, polyoxyethylenated and/or polyoxypropylenated $C_8-C_{22}$ aliphatic alcohols, ethylene oxide-propylene oxide block copolymers, optionally polyoxyethylenated carboxamides, and the like.

The usual additives which take part in the composition of detergent formulations for washing in a dishwasher can also be present.

Mention may in particular be made, among these, of:

builders (agents which improve the surface properties of surfactants) of the type:
organic phosphonates, such as those of the Dequest® range from Monsanto, in a proportion of 0 to 2% of the total detergent formulation weight, expressed on a dry basis, nitriloacetic acid, N,N-dicarboxymethyl-2-aminopentanedioic acid, ethylenediaminetetraacetic acid or diethylenetriaminepentaacetic acid, in a proportion of 0 to 10% of the total detergent formulation weight, expressed on a dry basis, citric acid, gluconic acid or tartaric acid or their salts, in a proportion of 0 to 10% of the total detergent formulation weight, expressed on a dry basis, bleaching agents of the following type: perborates, percarbonates, optionally in combination with N,N,N',N'-tetraacetylethylenediamine (TAED), or chlorinated products of the chloroisocyanurate type, in a proportion of 0 to 30% of the total weight of the said detergent formulation, expressed on a dry basis, cleaning auxiliaries of the following type: copolymers of acrylic acid and of maleic anhydride or acrylic acid homopolymers, in a proportion of 0 to 10%, alkali metal silicates with a molar ratio $SiO_2/Na_2O$ of the order of 1 to 3.5, as corrosion-inhibiting agents for metals, in an amount which can range up to approximately 50% of the total weight of the said detergent formulation, expressed on a dry basis, alkaline agents, such as alkali metal carbonates, bicarbonates or sesquicarbonates, or cogranules of alkali metal carbonate and of alkali metal silicate with a molar ratio $SiO_2/Na_2O$ of the order of 1.5 to 3.5, with a carbonate/silicate ratio by weight of the order of 5/95 to 45/55, comprising water according to a water/silicate, expressed on a dry basis, ratio by weight of at least 33/100, in a proportion of 0 to 50% of the total weight of the said formulation, expressed on a dry basis, fillers of the type of sodium sulphate for powder detergents in a proportion of 0 to 50% of the total weight of the said composition, expressed on a dry basis, various other additives, such as enzymes, in an amount which can range up to 5% of the total weight of the said formulation, expressed on a dry basis, fragrances, colorants, agents for inhibiting the corrosion of metals, agents for suspending dirt, and the like.

The detergent compositions for washing machines generally comprise:

surface-active agents, in amounts corresponding to approximately 3–40% by weight with respect to the detergent composition, chosen from the anionic, cationic, nonionic, zwitterionic or amphoteric surface-active agents, alone or in combination, mentioned in the description of the fluids for cleaning wells. Reference may therefore be made thereto.

adjuvants for improving the properties of surface-active agents (builders) in amounts corresponding to approximately 5–50%, preferably to approximately 5–30%, by weight for the liquid detergent formulations or to approximately 10–80%, preferably 15–50%, by weight for the powder detergent formulations, builders such as:

inorganic adjuvants (builders), such as alkali metal, ammonium or alkanolamine polyphosphates (tripolyphosphates, pyrophosphates, orthophosphates or hexametaphosphates)

tetraborates or borate precursors silicates, in particular those exhibiting an $SiO_2/Na_2O$ ratio of the order of 1.6/1 to 3.2/1, and the lamellar silicates disclosed in U.S. Pat. No. 4,664,839 alkali metal or alkaline earth metal carbonates (bicarbonates or sesquicarbonates)

cogranules of hydrated alkali metal silicates and of alkali metal carbonates (sodium carbonate or potassium carbonate) which are rich in silicon atoms in the Q2 or Q3 form, which are disclosed in EP-A-488,868 crystalline or amorphous alkali metal (sodium or potassium) or ammonium aluminosilicates, such as zeolites A, P, X, and the like; zeolite A with a particle size of the order of 0.1–10 micrometers is preferred organic adjuvants (builders), such as water-soluble polyphosphonates (ethane-1-hydroxy-1,1-diphosphonates, salts of methylenediphosphonates, and the like)

water-soluble salts of carboxyl polymers or copolymers or their water-soluble salts, such as polycarboxylate ethers (oxydisuccinic acid and its salts, tartrate monosuccinic acid and its salts, or tartrate disuccinic acid and its salts)

hydroxypolycarboxylate ethers citric acid and its salts, mellitic acid or succinic acid and their salts salts of polyacetic acids (ethylenediaminetetraacetates, nitrilotriacetates or N-(2-hydroxyethyl) nitrilodiacetates)

($C_5$–$C_{20}$ alkyl)succinic acids and their salts (2-dodecenylsuccinates or laurylsuccinates)

polyacetal carboxylic esters polyaspartic acid, polyglutamic acid and their salts polyimides derived from the polycondensation of aspartic acid and/or of glutamic acid polycarboxymethylated derivatives of glutamic acid or of other amino acids bleaching agents, in amounts of approximately 0.1–20%, preferably approximately 1–10%, by weight, optionally in combination with bleaching activators in amounts of approximately 0.1–60%, preferably of approximately 0.5–40%, by weight, agents and activators such as bleaching agents, such as perborates, such as sodium perborate monohydrate or tetrahydrate peroxygenated compounds, such as sodium carbonate peroxohydrate, pyrophosphate peroxohydrate, urea hydrogen peroxide, sodium peroxide or sodium persulphate preferably in combination with a bleaching activator generating in situ, in the detergent medium, a peroxycarboxylic acid; mention may be made, among these activators, of tetraacetylethylenediamine, tetraacetylmethylenediamine, tetraacetylglycoluril, sodium p-acetoxybenzenesulphonate, pentaacetylglucose, octaacetyllactose, and the like percarboxylic acids and their salts (known as "percarbonates"), such as magnesium monoperoxyphthalate hexahydrate, magnesium meta-chloroperbenzoate, 4-nonylamino-4-oxoperoxybutyric acid, 6-nonylamino-6-oxoperoxycaproic acid, diperoxydodecanedioic acid, the nonylamide of peroxysuccinic acid, or decyldiperoxysuccinic acid.

These agents can be used in combination with at least one of the antisoiling or antiredeposition agents mentioned hereinbelow.

Non-oxygenated bleaching agents, which act by photoactivation in the presence of oxygen, can also be mentioned, agents such as sulphonated zinc and/or aluminium phthalocyanines antisoiling agents, in amounts of approximately 0.01–10%, preferably approximately 0.1–5% and very particularly of the order of 0.2–3% by weight, agents such as cellulose derivatives, such as cellulose hydroxy ethers, methylcellulose, ethylcellulose, hydroxypropyl methylcellulose or hydroxybutyl methylcellulose poly(vinyl ester)s grafted onto polyalkylene back-bones, such as poly(vinyl acetate)s grafted onto polyoxyethylene backbones (EP-A-219,048)

poly(vinyl alcohol)s polyester copolymers based on ethylene terephthalate and/or propylene terephthalate and polyoxyethylene terephthalate units, with an ethylene terephthalate and/or propylene terephthalate (number of units)/ polyoxyethylene terephthalate (number of units) molar ratio of the order of 1/10 to 10/1, preferably of the order of 1/1 to 9/1, the polyoxyethylene terephthalates exhibiting polyoxyethylene units having a molecular weight of the order of 300 to 5000, preferably of the order of 600 to 5000 (U.S. Pat. No. 3,959,230, U.S. Pat. No. 3,893,929, U.S. Pat. No. 4,116,896, U.S. Pat. No. 4,702,857 and U.S. Pat. No. 4,770,666)

sulphonated polyester oligomers, obtained by sulphonation of an oligomer derived from ethoxylated allyl alcohol, from dimethyl terephthalate and from 1,2-propanediol, exhibiting from 1 to 4 sulphonate groups (U.S. Pat. No. 4,968,451)

polyester copolymers based on propylene terephthalate and polyoxyethylene terephthalate units which are terminated by ethyl or methyl units (U.S. Pat. No. 4,711, 730) or polyester oligomers which are terminated by alkylpolyethoxy groups (U.S. Pat. No. 4,702,857) or anionic sulphopolyethoxy (U.S. Pat. No. 4,721,580) or sulphoaroyl (U.S. Pat. No. 4,877,896) groups sulphonated polyester copolymers derived from terephthalic, isophthalic and sulphoisophthalic acid, anhydride or diester and from a diol (FR-A-2,720,399)

antiredeposition agents, in amounts of approximately 0.01–10% by weight for a powder detergent composition and of approximately 0.01–5% by weight for a liquid detergent composition, agents such as ethoxylated monoamines or polyamines, or polymers of ethoxylated amines (U.S. Pat. No. 4,597,898, EP-A-11,984)

carboxymethylcellulose sulphonated polyester oligomers obtained by condensation of isophthalic acid, of dimethyl sulphosuccinate and of diethylene glycol (FR-A-2,236,926)

polyvinylpyrrolidones iron- and magnesium-chelating agents, in amounts of the order of 0.1–10%, preferably of the order of 0.1–3%, by weight, agents such as aminocarboxylates, such as ethylenediaminetetraacetates, hydroxyethylethylenediaminetriacetates or nitrilotriacetates aminophosphonates, such as nitrilotris(methylenephosphonates)

polyfunctional aromatic compounds, such as dihydroxydisulphobenzenes polymeric dispersing agents, in an amount of the order of 0.1–7% by weight, in order to control the calcium and magnesium hardness, agents such as water-soluble salts of polycarboxylic acids with a molecular mass of the order of 2000 to 100,000, obtained by polymerization or copolymerization of ethylenically unsaturated carboxylic acids, such as acrylic acid, maleic acid or anhydride, fumaric acid, itaconic acid, aconitic acid, mesaconic acid, citraconic acid or methylenemalonic acid, and very particularly polyacrylates with a molecular mass of the order of 2000 to 10,000 (U.S. Pat. No. 3,308,067) or copolymers of acrylic acid and of maleic anhydride with a molecular mass of the order of 5000 to 75,000 (EP-A-66,915)

poly(ethylene glycol)s with a molecular mass of the order of 1000 to 50,000 fluorescence agents, in an amount of approximately 0.05–1.2% by weight, agents such as derivatives of stilbene, pyrazoline, coumarin, fumaric acid, cinnamic acid, azoles, methinecyanines, thiophenes, and the like ("The Production and Application of Fluorescent Brightening Agents", M. Zahradnik, published by John Wiley & Sons, New York, 1982)

other foam-suppressant agents, in amounts which can range up to 5% by weight, agents such as $C_{10}$–$C_{24}$ fatty monocarboxylic acids or their alkali metal, ammonium or alkanolamine salts, or fatty acid triglycerides saturated or unsaturated, aliphatic, alicyclic, aromatic or heterocyclic hydrocarbons, such as paraffins or waxes N-alkylaminotriazines monostearyl phosphates or monostearyl alcohol phosphates polyorganosiloxane oils or resins, optionally combined with silica particles softeners, in amounts of approximately 0.5–10% by weight, softeners such as clays enzymes, in an amount which can range up to 5 mg by weight, preferably of the order of 0.05–3 mg, of active enzyme/g of detergent composition, enzymes such as proteases, amylases, lipases, cellulases or peroxydases (U.S. Pat. No. 3,553,139, U.S. Pat. No. 4,101,457, U.S. Pat. No. 4,507,219 and U.S. Pat. No. 4,261,868)

other additives, such as alcohols (methanol, ethanol, propanol, isopropanol, propanediol, ethylene glycol or glycerol)

buffer agents fragrances pigments.

The detergent compositions for industrial and institutional detergency generally comprise nonionic surface-active agents (in a proportion of 0.05 to 50%, preferably of 0.1 to 20%, of the formulation), such as polyoxyalkylenated (polyoxyethylenated, polyoxypropylenated or polyoxybutylenated) alkylphenols, the alkyl substituent of which is $C_6$–$C_{12}$, comprising from 5 to 25 oxyalkylene units; mention may be made, by way of example, of Triton X-45, Triton X-114, Triton X-100 or Triton X-102, sold by Röhm & Haas Co.;

glucosamides, glucamides or glycerolamides;

polyoxyalkylenated $C_8$–$C_{22}$ aliphatic alcohols comprising from 1 to 25 oxyalkylene (oxyethylene or oxypropylene) units; mention may be made, by way of example, of Tergitol 15-S-9 or Tergitol 24-L-6 NMW, sold by Union Carbide Corp., Neodol 45-9, Neodol 23-65, Neodol 45-7 or Neodol 45-4, sold by Shell Chemical Co., or Rhodasurf IDO60, Rhodasurf LA90 or Rhodasurf IT070, sold by Rhône-Poulenc;

amine oxides, such as ($C_{10}$–$C_{18}$ alkyl)dimethylamine oxides or ($C_8$–$C_{22}$ alkoxy)ethyldihydroxyethylamine oxides;

the alkylpolyglycosides disclosed in U.S. Pat. No. 4,565,647;

$C_8$–$C_{20}$ fatty acid amides;

ethoxylated fatty acids;

ethoxylated amines;

amphoteric and zwitterionic surface-active agents (in a proportion of 0.05 to 50%, preferably of 0.1 to 20%, of the formulation), such as alkyl dimethyl betaines, alkyl amidopropyldimethyl betaines, alkyl dimethyl sulphobetaines or alkyl amidopropyldimethyl sulphobetaines, such as Mirataine CBS sold by Rhône-Poulenc, or the condensation products of fatty acids and of protein hydrolysates alkyl amphoacetates or alkyl amphodiacetates for which the alkyl group comprises from 6 to 20 carbon atoms.

cationic surface-active agents (in a proportion of 0.05 to 50%, preferably of 0.1 to 20%, of the formulation), such as alkylammonium salts of formula $R^1R^2R^3R^4N^+X^-$ where $X^-$ represents a halogen, $CH_3SO_4^-$ or $C_2H_5SO_4^-$ ion $R^1$ and $R^2$ are alike or different and represent a $C_1$–$C_{20}$ alkyl radical or an aryl or benzyl radical $R^3$ and $R^4$ are alike or different and represent a $C_1$–$C_{20}$ alkyl radical, an aryl or benzyl radical or an ethylene oxide and/or propylene oxide condensate ($CH_2$ $CH_2O)_x$—($CH_2CHCH_3O)_y$—H, where x and y range from 0 to 30 and are never simultaneously zero, such as Rhodaquat TFR, sold by Rhône-Poulenc.

anionic surface-active agents (in a proportion of 0.05 to 50%, preferably of 0.1 to 20%, of the formulation), such as alkyl ester sulphonates of formula R—CH($SO_3$M)-COOR', where R represents a $C_{8-20}$, preferably $C_{10}$–$C_{16}$, alkyl radical, R' a $C_1$–$C_6$, preferably $C_1$–$C_3$, alkyl radical and M an alkali metal cation (sodium, potassium or lithium), a substituted or unsubstituted ammonium (methyl-, dimethyl-, trimethyl- or tetramethylammonium, dimethylpiperidinium, and the like) cation or a cation derived from an alkanolamine (monoethanolamine, diethanolamine, triethanolamine, and the like). Mention may very particularly be made of the methyl ester sulphonates for which the R radical is a $C_{14}$–$C_{16}$ radical;

alkyl sulphates of formula $ROSO_3M$, where R represents a $C_5$–$C_{24}$, preferably $C_{10}$–$C_{18}$, alkyl or hydroxyalkyl radical, M representing a hydrogen atom or a cation with the same definition as above, and their ethoxylated (EO) and/or propoxylated (PO) derivatives exhibiting an average of 0.5 to 30, preferably of 0.5 to 10, EO and/or PO units;

alkylamide sulphates of formula $RCONHR'OSO_3M$, where R represents a $C_2$–$C_{22}$, preferably $C_6$–$C_{20}$, alkyl radical, R' represents a $C_2$–$C_3$ alkyl radical, M representing a hydrogen atom or a cation with the same definition as above, and their ethoxylated (EO) and/or propoxylated (PO) derivatives exhibiting an average of 0.5 to 60 EO and/or PO units;

salts of saturated or unsaturated $C_8$–$C_{24}$, preferably $C_{14}$–$C_{20}$, fatty acids, $C_9$–$C_{20}$ alkylbenzenesulphonates, primary or secondary C8–$C_{22}$ alkylsulphonates, alkylglycerol sulphonates, the sulphonated polycarboxylic acids disclosed in GB-A-1,082,179, paraffin sulphonates, N-acyl-N-alkyltaurates, alkyl phosphates, isethionates, alkylsuccinamates, alkylsulphosuccinates, the monoesters or diesters of sulphosuccinates, N-acylsarcosinates, alkylglycoside sulphates or polyethoxycarboxylates the cation being an alkali metal (sodium, potassium, lithium), a substituted or unsubstituted ammonium residue (methyl-, dimethyl-, trimethyl- or tetramethylammonium, dimethylpiperidinium, and the like) or a residue derived from an alkanolamine (monoethanolamine, diethanolamine, triethanolamine, and the like);

phosphate alkyl or alkylaryl esters, such as Rhodafac RA600, Rhodafac PA15 or Rhodafac PA23, sold by Rhône-Poulenc.

organic detergency adjuvants (builders) (in a proportion of 0.1 to 50%, preferably of 0.1 to 20%, of the formulation), such as water-soluble polyphosphonates water-soluble salts of carboxyl polymers or copolymers, such as polycarboxylate or hydroxypolycarboxylate ethers citrates salts of polyacetic acids (ethylenediaminetetraacetates, nitrilotriacetates, such as Nervanaid NTA $Na_3$, sold by Rhône-Poulenc, or N-(2-hydroxyethyl) nitrilodiacetates)

salts of ($C_5$–$C_{20}$ alkyl)succinic acids polyacetal carboxylic esters salts of polyaspartic or polyglutamic acids inorganic detergency adjuvants (builders) (in a proportion of 0.1 to 50%, preferably of 0.1 to 20%, of the formulation), such as alkali metal, ammonium or alkanolamine polyphosphates, such as Rhodiaphos HPA3.5, sold by Rhône-Poulenc alkali metal pyrophosphates silicates alkali metal or alkaline earth metal carbonates cogranules of hydrated alkali metal silicates and of alkali metal (sodium or potassium) carbonates disclosed in EP-A-488,868, such as Nabion 15, sold by Rhône-Poulenc hydrotropic agents in the case of liquid formulae, such as sodium cumene- or xylenesulphonate or phosphate esters, such as Rhodafac HA70, sold by Rhône-Poulenc.

The following examples are given by way of illustration.

Defoaming Test

Principle of the Test

The test consists in observing, for 15 minutes, the foam formed after stirring a test solution comprising a foaming agent and a defoaming agent for 5 minutes and in comparing the results with those observed in the absence of defoaming agent (reference solution).

Procedure 900 g of test solution are placed in a 2 liter stainless steel beaker (height of 190 mm and diameter of 120 mm) which has been cleaned beforehand and which is held firm with respect to a stirrer system composed of a paddle (Raynerie centripetal paddle with a diameter of 40 mm, driven by a Raynerie stirrer of Turbotest 1044 type) and of a baffle.

The stirrer is switched on at 2000 revolutions/minute for 5 minutes.

The beaker is subsequently removed from the stirrer system; its contents are poured as quickly as possible into a 2 liter graduated measuring cylinder (NF B 35302), so that the liquid and the foam flow along the wall of the measuring cylinder.

The clock is started and the volume of foam (situated between the top level and the bottom level) is recorded after 0, 1, 2, 3, 4, 5, 10 and 15 minutes.

These measurements are made with the reference solution and then with a solution comprising the defoaming agent to be tested.

Expression of the Results

The latter can be expressed either by the volume of foam in ml observed or by measurement of the efficiency parameter E in %, calculated as follows:

$$E=[So-Sc]/So \times 100$$

So being the area of the curve expressing the volume of foam formed with the reference solution as a function of the time (0 to 15 minutes), Sc being the area of the curve expressing the volume of foam formed with the tested solution as a function of the time (0 to 15 minutes).

The efficiency of the defoaming agent increases as Sc decreases.

EXAMPLE 1

Preparation of Nopol 3 PO/6 EO/15 PO

Nopol of formula (II') (1 kg, 6 mol) and an aqueous potassium hydroxide solution (50%, 17.7 g) are introduced into a 12 liter alkoxylation reactor. The reaction mixture is dehydrated at 120° C. under a nitrogen stream.

The mixture is subsequently heated to 165° C. and propylene oxide (1.045 kg, 3 molar equivalents) is introduced. At the end of the addition of propylene oxide, ethylene oxide (1.586 kg, 6 molar equivalents) is introduced.
At the end of the addition of ethylene oxide, propylene oxide (5.227 kg, 15 molar equivalents) is introduced. The reaction mixture is then cooled and neutralized by addition of acetic acid until a pH of 7 is obtained. The liquid is filtered through adsorbant earth (Clarcel DIC).
A clear fluid liquid is obtained.
A solution in butyl digol comprising 10% by weight of the said liquid prepared above exhibits a cloud temperature of 35.5° C.

EXAMPLE 2
Preparation of Arbanol 2 PO/7.5 EO/S PO

Arbanol of formula (II″) (1 kg, 5 mol) and an aqueous potassium hydroxide solution (50%, 9.4 g) are introduced into a 6 liter alkoxylation reactor. The reaction mixture is dehydrated at 120° C. under a nitrogen stream.
The mixture is subsequently heated to 165° C. and propylene oxide (0.58 kg, 2 molar equivalents) is introduced. At the end of the addition of propylene oxide, ethylene oxide (1.652 kg, 7.5 molar equivalents) is introduced.
At the end of the addition of ethylene oxide, propylene oxide (1.452 kg, 5 molar equivalents) is introduced. The reaction mixture is then cooled and neutralized by addition of acetic acid until a pH of 7 is obtained. The liquid is filtered through adsorbant earth (Clarcel DIC).
A clear fluid liquid is obtained.
A solution in distilled water comprising 1% by weight of the said liquid prepared above exhibits a cloud temperature of 32.5° C.

EXAMPLE 3
Defoaming of Aqueous Media for Degreasing Metal Surfaces (Sheets, Platforms) in Alkaline Medium
-Defoaming Test- The defoaming test described above is carried out at 50° C. on an aqueous medium composed of 20 g/l of an alkaline detergent, comprising 45% of active material, composed of equal amounts by weight of potash, of sodium metasilicate (Simet GA5, granules of anhydrous metasilicate and of metasilicate pentahydrate, sold by Rhône-Poulenc) and of tetrapotassium pyrophosphate 1 g/l of foaming Igepal NP10 (nonylphenol comprising 10 oxyethylene units)

0.5 g/l of defoaming surface-active agent to be tested.

The surface-active systems tested are as follows:

1 g/l of Igepal NP10 alone (reference)
1 g/l of Igepal NP10+0.5 g/l of Nopol 3 PO/6 EO/15 PO prepared in Example 1
1 g/l of Igepal NP10+0.5 g/l of Nopol 7.5 EO/5.5 PO prepared as disclosed in WO 96/01245
1 g/l of Igepal NP10+0.5 g/l of Nopol 2 PO/5.1 EO prepared in Example 2–2.6 of WO 96/01245
1 g/l of Igepal NP10+0.5 g/l of Plurafac LF 431, a commercial defoaming agent (alcoholxEO/y PO—CH₃, sold by BASF)
1 g/l of Igepal NP10+0.5 g/l of Miravon B12 DF, a commercial defoaming agent (alcoholxEO/y PO, sold by Rhône-Poulenc).

The cloud temperatures of the alkaline solutions obtained are as follows:

| Alkaline solution comprising | Cloud temperatures |
| --- | --- |
| 1 g/l of Igepal NP10 alone | 61° C. |
| 1 g/l of Igepal NP10 + 0.5 g/l of Nopol 3 PO/6 EO/15 PO | 42° C. |
| 1 g/l of Igepal NP10 + 0.5 g/l of Nopol 7.5 EO/5.5 PO | 55° C. |
| 1 g/l of Igepal NP10 + 0.5 g/l of Nopol 2 PO/5.1 EO | 45° C. |
| 1 g/l of Igepal NP10 + 0.5 g/l of Plurafac LF 431 | 47° C. |
| 1 g/l of Igepal NP10 + 0.5 g/l of Miravon B12 DF | 41° C. |

The volumes of foam measured as a function of the time are given in the table below:

| Surfactant system | Volume of foam in ml after | | | | | | | |
| --- | --- | --- | --- | --- | --- | --- | --- | --- |
| | 30″ | 1 min | 2 min | 3 min | 4 min | 5 min | 10 min | 15 min |
| NP 10 alone | 1540 | 1280 | 1020 | 940 | 780 | 730 | 650 | 520 |
| NP 10 + Nopol 3 PO/6 EO/15 PO | 180 | 160 | 140 | 120 | 100 | 80 | 60 | 60 |
| NP 10 + Plurafac LF 431 | 500 | 400 | 240 | 170 | 130 | 110 | 80 | 60 |
| NP 10 + Miravon B12 DF | 160 | 140 | 90 | 80 | 70 | 70 | 60 | 50 |
| NP 10 + Nopol 7.5 EO/5.5 PO | 1600 | 1400 | 1200 | 1100 | 900 | 830 | 750 | 600 |
| NP 10 + Nopol 2 PO/5.1 EO | 1500 | 1200 | 950 | 850 | 750 | 650 | 570 | 460 |

-Degreasing Test-
Greasing

Predegreased steel plates with the trademark "Q-Panel" Stock No. R-36, type "Dull matt finish", with dimensions of 0.8×76×152 mm, are immersed for 2 minutes in a whole lubricating oil formulated for rolling (of automobile steel sheets) with the trade-mark Quaker 6130 N from Quaker Chemicals and are then suspended for draining for 24 hours.
Cleaning and Rinsing The greased plates are introduced into a Ciemme Laro 350 machine for degreasing by spraying. The degreasing temperature is 45° C. and the pressure is 2 bar.
A basic degreasing medium (pH 12–13) is prepared by diluting an aqueous detergent comprising 45% by weight of active material, composed of equal amounts by weight of potash, of sodium metasilicate (Simet GA5, granules of anhydrous metasilicate and of metasilicate pentahydrate, sold by Rhône-Poulenc) and of tetrapotassium pyrophosphate, in water to 8 g/l and adding 1.5 g/l of surface-active system to be tested, i.e.

1.5 g/l of Igepal NP10 alone
1.5 g/l of a system composed of 50% of Igepal NP10 and of 50% of Nopol 3 PO/6 EO/15 PO
1.5 g/l of a system composed of 50% of Igepal NP10 and of 50% of Miravon B12 DF.

The immersion time of the plates in the degreasing solution is chosen in order to allow complete degreasing, that is to say corresponding, after rinsing the plates under a stream of ordinary water for 5 seconds on each face (flow rate=2 1/min; temperature 15–17° C.), to the grading 4 (complete covering of both faces of the plates by a continuous film of water).

Results

The time necessary in order to arrive at complete degreasing of the plates (grading 4) is shown in the following table.

| Surfactant | Time in seconds in order to achieve the grading 4 |
|---|---|
| Igepal NP10 | 30 |
| 50% Igepal NP10 + 50% Nopol 3 PO/6 EO/15 PO | 30 |
| 50% Igepal NP10 + 50% Miravon B12 DF | 45 |

It is found that the Nopol 3 PO/6 EO/15 PO according to the invention has made it possible to completely defoam the medium without damaging the performance of the degreasing surface-active agent.

EXAMPLE 4

Defoaming of Aqueous Media Comprising Albumin (Household Detergency in Dishwashers)

The defoaming test described above is carried out on an aqueous medium comprising

| albumin (powdered egg albumin from Prolabo foaming agent) | 0.66 g/l |
|---|---|
| sodium carbonate | 3.83 g/l |
| defoaming agent to be tested | 0.33 g/l |

The surface-active agents tested are

Nopol 3 PO6 EO/15 PO prepared in Example 1
Arbanol 2 PO/7.5 EO/5 PO prepared in Example 2
Plurafac LF 403 (defoaming alkoxylated linear alcohol from BASF)
Miravon B12 DF
Nopol 3 PO/6 EO prepared as disclosed in WO 96/01245

The results obtained are as follows:

| Defoaming agent | Efficiency E % |
|---|---|
| Nopol 3 PO/6 EO/15 PO | 99.1 |
| Arbanol 2 PO/7.5 EO/5 PO | 81.4 |
| Plurafac LF 403 | 94.4 |
| Miravon B12 DF | 92.05 |
| Nopol 3 PO/6 EO | 66.59 |

EXAMPLE 5

Defoaming of Aqueous Media Comprising Milk (Industrial and Institutional Detergency)

The defoaming test described above is carried out on an aqueous medium comprising

| skimmed milk powder with 0% fat (Bridel milk spray foaming agent) | 25 g/l |
|---|---|
| soda | 20 g/l |
| defoaming surface-active agent to be tested | 0.5 g/l |

The surface-active agents tested are

Nopol 3 PO/6 EO/15 PO
Arbanol 2 PO/7.5 EO/5 PO prepared in Example 2
Triton DF16 (defoaming polyethoxylated linear alcohol from Union Carbide)
Miravon B12 DF The results obtained are as follows:

| Defoaming agent | Efficiency E % |
|---|---|
| Nopol 3 PO/6 EO/15 PO | 95.5 |
| Arbanol 2 PO/7.5 EO/5 PO | 96.3 |
| Triton DF16 | 60 |
| Miravon B12 DF | 97 |

EXAMPLE 6

The defoaming test is carried out in a machine for washing laundry with a vertical window of AEG 2050 type, under the real conditions of a washing cycle at 95° C.

Use is made, in a proportion of 5 g/l, of a washing powder comprising the following components

| Glucopon 600 CS/UP/PF (as is) from Henkel (foaming agent) (polyglucoside exhibiting a $C_{12}$–$C_{14}$ linear chain, comprising 50–53% of active material) | 12% |
|---|---|
| Perborate monohydrate | 15% |
| TAED (92% by weight aqueous solution of tetraacetylethylenediamine) | 5% |
| Nabion from Rhône-Poulenc (cogranules of sodium silicate and of sodium carbonate) | 38% |
| Sodium carbonate | 8% |
| Sodium sulphate | 10.6% |
| Sokalan CP5 from BASF (acrylic/maleic copolymer) | 5% |
| Dequest 2016 from Monsanto (phosphonate) | 1.6% |
| Carboxymethylcellulose | 1.5% |
| Esperase | 0.15% |
| Savinase | 0.15% |
| Defoaming agent to be tested | 3% |

The surface-active agents tested are as follows

Nopol 3 PO/6 EO/15 PO
Miravon B12 DF
Nopol 3 PO/6 EO

A standardized washing load, composed of 10 cotton cloths, is introduced via the window and programme 5 of the washing machine is started, so as to operate at a constant water content.

At the end of this programme, 65 g of washing powder are introduced and the 95° C. without prewash programme is started.

The volume of foam formed during the programme is measured visually.

Figure 3:
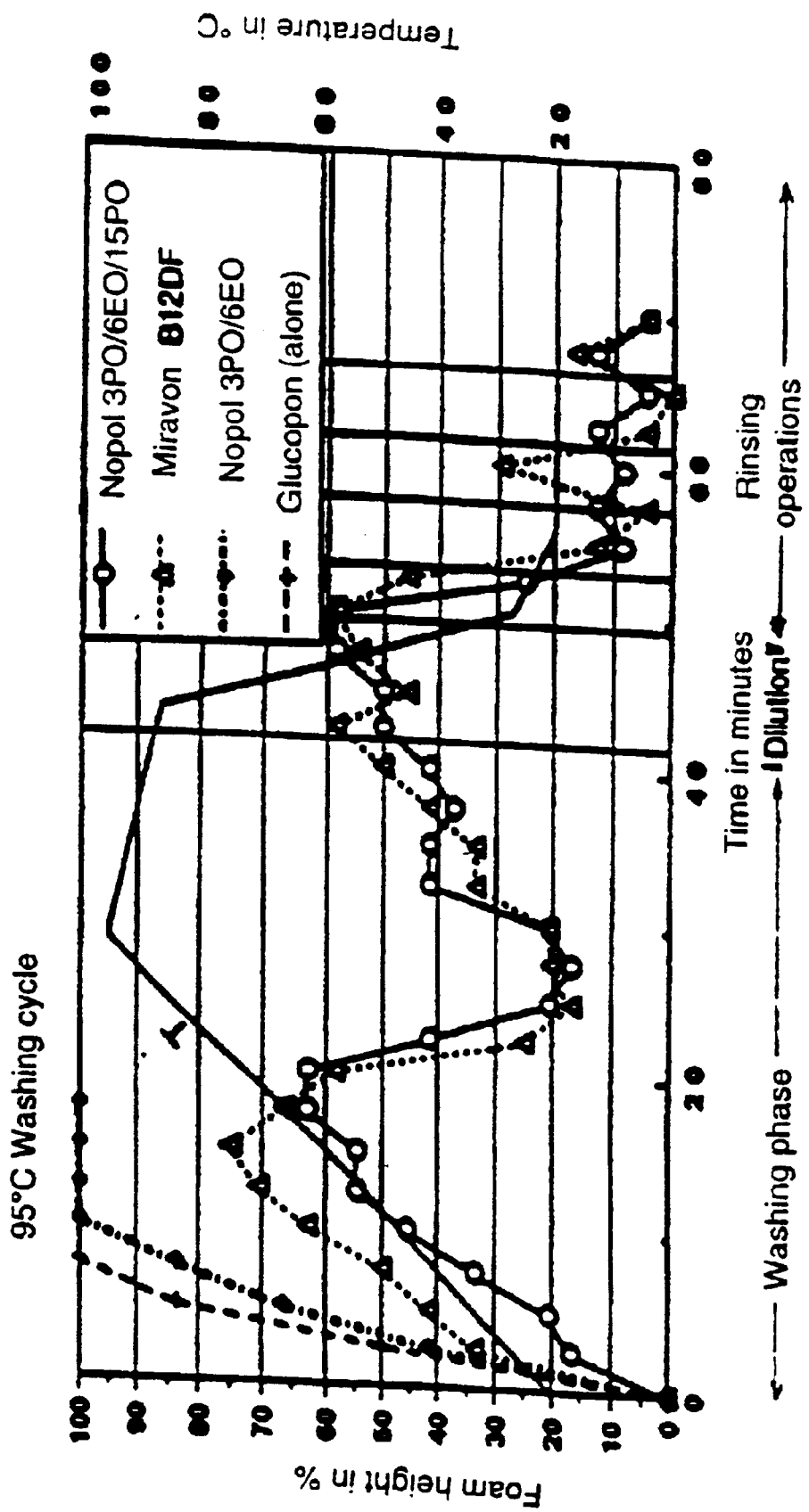
FIG. 3 represents the foam height, expressed as % of window height, observed as a function of time for the four different defoaming tests of example 6.

The results are recorded on the graph in FIG. 3, which represents the foam height, expressed as % of window height, observed as a function of time. The temperature profile of the entire operation also appears on this graph.

The results show that

Nopol 3 PO/6 EO/15 PO efficiently defoams the detergent formula; it is at least as efficient at Miravon B12 DF without defoaming agent or in the presence of Nopol 3 PO6 EO as defoaming agent, the machine overflows, which requires the test to be halted.

What is claimed is:

1. A polyalkoxylated terpenic compound of formula:

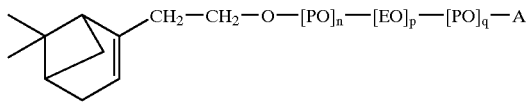

wherein:

A=H, n is from 2 to 4, p is from 3 to 20, and q is from 5 to 20.

2. A polyalkoxylated terpenic compound according to claim 1, wherein the mean values of n, p and q are chosen so that a 1% by weight solution in distilled water of said compound exhibits a cloud point of less than 40° C.

3. A process for the preparation of a polyalkoxylated terpenic compound as defined in claim 1 comprising the steps of:

a) successively carrying out polyalkoxylation reactions of a reactant of formula:

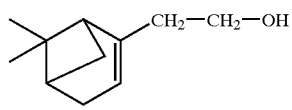 (II')

first with propylene oxide then, with ethylene oxide (EO) of formula:

and, then with propylene in order to obtain said polyalkoxylated terpenic compound.

4. A process for defoaming an aqueous media forming foams comprising the step of adding to said media at least one polyalkoxylated terpenic compound as defined in claim 1.

5. A process according to claim 4, wherein said aqueous media, are aqueous media for degreasing metal sheets in alkaline medium, aqueous media for degreasing drilling platforms, aqueous media employed for cleaning oil drilling wells drilled by means of oil-based fluids, aqueous detergent media used in household detergency, aqueous detergent media used in industrial detergency, or aqueous detergent media used in institutional detergency.

6. Aqueous compositions for degreasing metal surfaces in alkaline medium or oil drilling wells or detergents comprising at least one polyalkoxylated terpenic compound as defined in claim 1.

* * * * *